United States Patent [19]

Hoelderich et al.

[11] Patent Number: 4,922,025

[45] Date of Patent: May 1, 1990

[54] PREPARATION OF ORGANOPHOSPHORUS COMPOUNDS

[75] Inventors: Hoelderich Wolfgang, Frankenthal; Michael Hesse, Ludwigshafen; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 216,612

[22] Filed: Jul. 8, 1988

[30] Foreign Application Priority Data

Jul. 22, 1987 [DE] Fed. Rep. of Germany ....... 3724238

[51] Int. Cl.$^5$ .............................................. C07F 9/53
[52] U.S. Cl. ........................................... 568/14; 568/8
[58] Field of Search ..................................... 568/8, 14

[56] References Cited

U.S. PATENT DOCUMENTS

| | | | |
|---|---|---|---|
| 2,957,931 | 10/1960 | Hamilton et al. | 260/403 |
| 3,855,311 | 12/1974 | Staendeke | 568/8 |
| 3,954,859 | 5/1976 | Jurewicz et al. | 260/543 P |
| 4,073,810 | 2/1978 | Hestermann et al. | 568/8 |
| 4,717,785 | 1/1988 | Paxson | 585/823 |

FOREIGN PATENT DOCUMENTS 673451 6/1952 United Kingdom .

OTHER PUBLICATIONS

J. Chem. Soc. 1083 (1963).
General Chemistry, 5th Edition, William H. Nebergall et al., D.C. Heath and Company, Lexington, MA, Toronto London.

*Primary Examiner*—John Doll
*Assistant Examiner*—Stuart L. Hendrickson
*Attorney, Agent, or Firm*—Keil & Weinkauf

[57] ABSTRACT

Organophosphorus compounds are prepared by reacting an unsaturated compound, such as a straight-chain, branched or cyclic olefin or a diene having conjugated or nonconjugated double bonds, with a phosphine by a process in which phosphine and/or phosphine-containing compounds are subjected to an addition reaction with the unsaturated compounds in the presence of a solid heterogeneous catalyst. Particularly suitable heterogeneous catalysts are zeolites and phosphates.

6 Claims, No Drawings

PREPARATION OF ORGANOPHOSPHORUS COMPOUNDS

The present invention relates to a process for the preparation of organophosphorus compounds.

A wide variety of possible methods exist for the synthesis of organophosphorus compounds. For example, triphenylphosphine can be prepared by subjecting benzene and diphenylchlorophosphine to a Friedel-Crafts reaction (JP 59/116 387). For the synthesis of alkylphosphines, in particular methylphosphines, white phosphorus can be reacted with tertiary and secondary amines (DE 2 730 742) or phosphine with a tertiary amine and an alkyl halide (DE 2 727 390 and DE 2 407 461) or white phosphorus can be reacted with an alkyl halide in the presence of HCl (DE 2 255 395), mixtures of primary, secondary and tertiary phosphines being obtained in moderate yields. The reaction of metal phosphides with alkyl halides (J. Org. Chem. 42 (1977), 3247-3251 or J. Inorg. Nucl. Chem. 35 (8) (1973), 2659) or water (Inorg. Synthn. 16 (1976), 161-163), as well as the reaction of tetraalkyldiphosphine sulfides with $LiAlH_4$ (eg. Chem. Ber. 95 (1962), 64) or with tributylphosphine (Inorg. Synth. 21 (1982), 180-181), makes it possible to prepare various organophosphorus compounds. The Michaelis-Arbuzow rearrangement reaction (eg. Inorg. Nucl. Chem. 31 (1969), 3684) can be used for the preparation of primary phosphines, mainly methylphosphine. Furthermore, the Grignard reaction of triphenyl phosphites leads to alkylphosphines (Syn. Reactiv. Inorg. Metal-Org. Chem. 4 (2) (1974), (149).

The disadvantages of these known preparation processes are that the desired compound or a mixture of compounds which is difficult to separate is usually obtained over a plurality of reaction steps. The use of white phosphorus as a starting material presents problems with regard to handling, as does the use of metal phosphites, which are not cheaply available. Furthermore, phosphines having mixed substituents are very difficult to synthesize by the conventional processes.

It is also known that alkylphosphines can be prepared from $PH_3$ and aliphatic monoolefins in the presence of peroxides as free radical formers (German Patent 899,040 and U.S. Patent 2,957,931) or under UV irradiation (J. Chem. Soc. (1963), 1083). These processes are only of limited use in the preparation of alkylphosphines and, when they can be used, give only moderate yields.

It is an object of the present invention to synthesize organophosphorus compounds in high yields from cheap starting materials by a simple synthesis which takes place in one reaction step. It was also intended to find a simple possible synthesis for organophosphorus compounds having mixed substituents.

We have found that this object is achieved by a process for the preparation of organophosphorus compounds by reacting an unsaturated compound, such as a straight-chain, branched or cyclic olefin or a diene having conjugated or nonconjugated double bonds with a phosphine by a process in which phosphine and/or a phosphine-containing compound is subjected to an addition reaction with the unsaturated compound in the presence of a solid heterogeneous catalyst.

In the novel process, the requirements set at the outset for the reaction are met. In view of the prior art, the success of the process was particularly surprising since, because of the sensitivity of the phosphorus compounds used and those obtained to oxygen, temperature, etc., the reaction was not expected to take place readily and was certainly not expected to give such high conversions and selectivities. Furthermore, the novel process is very suitable for the synthesis of organophosphorus compounds having mixed substituents. The requirements which the catalysts used have to meet, such as catalyst life, time-on-stream, mechanical stability, activity and selectivity, are very readily met. This is all the more surprising since the highly sensitive phosphines used were expected to react with the catalyst.

The unsaturated compounds used are straightchain, branched or cyclic olefins and dienes having conjugated and nonconjugated double bonds.

Suitable olefins are isobutylene, propylene, ethylene, n-butene, cis- and trans-but-2-ene, pentenes, methylbutenes, hexenes, methylpentenes, ethylbutenes, cyclopentenes and cyclohexenes, and suitable dienes are isoprene, vinylcyclohexene, hexadienes and pentadienes.

Suitable phosphine-containing compounds are primary and secondary phosphines, diphosphanes, polyphosphanes and organophosphorus oxides.

Suitable primary phosphines are compounds of the formula $H_2PR$, where R is straight-chain or branched alkyl of 1 to 16 carbon atoms, eg. methyl, ethyl, propyl, isopropyl, n-butyl, isobutyl, tert-butyl, pentyl, hexyl, decyl and dodecyl, or cyclic alkyl radicals of 3 to 8 carbon atoms, eg. pentyl, hexyl or heptyl, or aryl or aralkyl or alkylaryl, which in turn may be substituted in the aromatic nucleus by substituents which are inert under the chosen reaction conditions, eg. phenyl, benzyl, phenylethyl, mesityl, toluyl, xyloyl, ethylphenyl, propylphenyl or phenylpropyl, or silyl radicals, eg. trimethylsilyl, triethylsilyl, dimethylphenylsilyl, dimethylethylsilyl or dimethylpropylsilyl, or amine radicals, eg. dimethylamine, diethylamine, methylethylamine, methylpropylamine or methylphenylamine radicals, or boryl radicals, eg. dimethylboryl, diethylboryl, methylpropylboryl or methylphenylboryl.

Suitable secondary phosphanes are compounds of the formula $HPRR^1$, where R and $R^1$ can be identical or different and may have the above meanings.

Suitable diphosphanes are compounds of the formula $RR^1P-PR^1R$, where one or more radicals are hydrogen and the remaining radicals R and $R^1$ may be identical or different and may have the above meadings. However, compounds which have 2-phosphino radicals and also possess a straight-chain or branched carbon chain between these radicals are also suitable.

Linear and cyclic polyphosphines, eg. triphosphines of the formula $RR^1P-PR-PR^{11}R$, where one or more radicals are hydrogen and the remaining radicals may have the above meanings, are suitable starting materials. A straight-chain or branched carbon chain may furthermore be present between the individual phosphino radicals.

Compounds of the formula $RR^1R^2 P(O)$ can be reacted as organophosphorus oxides in the process, and one or more of the radicals are hydrogen and the remaining radicals R, $R^1$ or $R^2$ may be identical or different and may have the above meanings.

The unsaturated compounds used are straightchain or branched olefins of 1 to 16 carbon atoms, eg. ethylene, propylene, n-butene, cis/trans-but-2-ene, isobutene, pentenes, methylbutenes, hexenes, methylpentenes, ethylbutenes, ethyloctenes, dodecenes, phenylpropene, styrene, ethylstyrene and isobutenylbenzene, and cyclic olefins, eg. cyclopentenes or cyclohexenes, and di- and polyenes having conjugated double bonds, eg. isoprene, vinylcyclohexene, hexadienes, pentadienes and butadienes.

The reactions according to equations 1 and 2 illustrate the invention

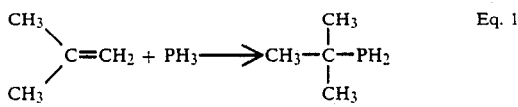

Eq. 1

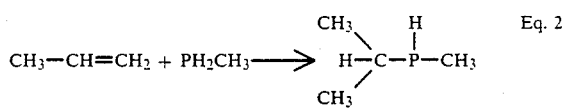

Eq. 2

The heterogeneous catalysts used in the novel process are preferably zeolite catalysts in acidic form. Zeolites are crystalline aluminosiltcates which have a highly ordered structure with a rigid three-dimensional network of $SiO_4$ and $AlO_4$ tetrahedra which are bonded by common oxygen atoms. The ratio of the Si and Al atoms to oxygen is 1 : 2 (cf. Ullmanns Encyclopädie d. techn. Chemie, 4th Edition, Volume 24, page 575 (1983)). The electrovalency of the aluminum-containing tetrahedra is balanced by the inclusion of cations in the crystal, for example an alkali metal or hydrogen ion. Cation exchange is possible. The voids between the tetrahedra are occupied by water molecules prior to dehydration by drying or calcination.

In the zeolites, other elements, such as B, Ga, Fe, Cr, V, As, Sb, Bi or Be, or mixtures of these may be incorporated, instead of aluminum, in the framework, or the silicon can be replaced by a tetravalent element, such as Ge, Ti, Zr or Hf.

Zeolites are divided into various groups, depending on their structure (cf. Ullmanns Encyclopädiae d. techn. Chemie, 4th Edition, Vol. 24, page 575 (1983)). For example, chains of tetrahedra form the zeolite structure in the mordenite group and sheets of tetrahedra form the zeolite structure in the chabasite group, whereas in the faujasite group the tetrahedra are arranged to form polyhedra, for example in the form of a cubooctahedron, which is composed of 4-membered rings and 6-membered rings. Depending on the bonding of the cubooctahedra, which results in cavities and pores of different sizes, a distinction is made between zeolites of type A, L, X and Y.

Suitable catalysts for the novel process are zeolites from the mordenite group, the fine-pore zeolites of the erionite and chabasite type and zeolites of the faujasite type, for example Y, X or L zeolites. This group of zeolites also includes the ultrastable zeolites of the faujasite type, ie. dealuminated zeolites. Processes for the preparation of such zeolites are described in Catalysis by Zeolites, Volume 5, from Studies in Surface Science and Catalysis, ed. B. Imelik et al., Elsevier Scientific Publishing Company 1980, page 203, and Crystal Structures of Ultra-stable Faujasites, Advances in Chemistry Series No. 101, American Chemical Society Washington DC, page 226 et seq (1971) and in U.S. Patent 4,512,961.

Zeolites of the pentasil type are particularly advantageous. They have a 5-membered ring consisting of $SiO_4$ tetrahedra as a common building block. They possess a high $SiO_2/Al_2O_3$ ratio and pore sizes which are between those of the zeolites of type X and Y (cf. Ullmanns Encyclopädie d. techn. Chem., 4th Edition, Vol. 24, 1983).

These zeolites may have different chemical compositions. They are aluminosilicate, borosilicate, iron silicate, beryllium silicate, gallium silicate, chromium silicate, arsenosilicate, antimony silicate and bismuth silicate zeolites or mixtures of these, and aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in polyamines, such as 1,6-hexanediamine or 1,3-propanediamine or triethylenetetramine solution, with or, in particular, without the addition of an alkali or alkaline earth, at from 100 to 220° C. under autogenous pressure. They also include the isotactic zeolites according to European Pat. No. 34,727 and 46,504. The aluminosilicate zeolites obtained have an $SiO_2/Al_2O_3$ ratio of from 10 to 40,000, depending on the amounts of starting materials chosen. Aluminosilicate zeolites of this type can also be synthesized in an ether medium, such as diethylene glycol dimethyl ether, in an alcoholic medium, such as methanol or butane-1,4-diol, or in water.

Borosilicate zeolites can be synthesized, for example, at from 90° to 200° C. under autogenous pressure by reacting a boron compound, eg. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. They include the isotactic zeolites according to European Pat. Nos. 34,727 and 46,504. Such borosilicate zeolites can also be prepared if the reaction is carried out in ether solution, eg. diethylene glycol dimethyl ether, or in alcoholic solution, eg. hexane-1,6-diol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth, at from 100° to 220° C. under autogenous pressure.

The silicon-rich zeolites ($SiO_2/Al_2O_3 \geq 10$) which can be used also include zeolites of the ZSM type, ferrierite, $Nu^{-1}$ and Silicalit ®.

The aluminosilicate, borosilicate and iron silicate zeolites thus prepared can be isolated, dried at from 100° to 160° C., preferably 110° C., and calcined at from 450° to 550° C. and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Very efficient catalysts are also obtained if the aluminosilicate or borosilicate zeolite isolated is molded directly after drying and is not subjected to calcination until after the molding procedure. The aluminosilicate and borosilicate zeolites prepared can be used in pure form, without a binder, as extrudates or tablets, examples of suitable extrusion or peptizing assistants being ethylcellulose, stearic acid, potato starch, formic acid, oxalic acid, acetic acid, nitric acid, ammonia, amines, silicoesters and graphite or mixtures of these.

If, because of its method of preparation, the zeolite is not in the catalytically active, acidic H form but, for example, in the Na form, the latter can be completely or partially converted into the desired H form by ion exchange, for example with ammonium ions, and subsequent calcination, or by treatment with acids.

If, when the zeolite catalysts are used according to the invention, deactivation occurs as a result of coking, it is advisable to regenerate the zeolites by burning off the coke deposit with air or with an air/$N_2$ mixture at from 400 to 550° C., preferably 500° C. As a result, the zeolites regain their initial activity.

By precoking, it is possible to adjust the activity of the catalyst to obtain optimum selectivity with respect to the desired reaction product.

In order to obtain very high selectivity, high conversion and a long catalyst life, it is advantageous to modify the zeolites. In a suitable method of modification, for example, the unmolded or molded zeolites are doped with metal salts by ion exchange or by impregnation. The metals used are alkali metals, such as Li, Cs or K, alkaline earth metals, such as Mg, Ca or Sr, metals of main groups 3, 4 and 5, such as Al, Ga, Ge, Sn, Pb or Bi, transition metals of subgroups 4 to 8, such as Ti, Zr, V, Nb, Cr, Mo, W, Mn, Re, Fe, Ru, Os, Co, Rh, Ir, Ni, Pd or Pt, transition metals of subgroups 1 and 2, such as Cu, Ag or Zn, and rare earth metals, such as La, Ce, Pr, Nd, Er, Yb and U.

The doping is advantageously carried out by a procedure in which, for example, the molded zeolite is initially taken in a riser tube and an aqueous or ammoniacal solution of a halide or of a nitrate of the metals described above is passed over the said zeolite at from 20° to 100° C. Ion exchange of this type may be carried out, for example, on the hydrogen, ammonium and alkali metal form of the zeolite. In another possible method for applying the metals to the zeolites, the zeolite material is impregnated with, for example, a halide, a nitrate or an oxide of the metals described above, in aqueous, alcoholic or ammoniacal solution. Both ion exchange and impregnation may be followed by one or more drying steps and, if desired, repeated calcination.

In a possible embodiment, for example, $Cu(NO_3)_2$. $3H_2O$ or $Ni(NO_3)_2$. $6H_2O$ or $Ce(NO_3)_3$ . $6H_2O$ or La-$NO_{32}$. $6H_2O$ or $Cs_2CO_3$ is dissolved in water and this solution is used to impregnate the molded or unmolded zeolite for a certain time (about 30 minutes). Any supernatant solution is freed from water in a rotary evaporator. Thereafter, the impregnated zeolite is dried at about 150° C. and calcined at about 550° C. This impregnation process can be carried out several times in succession in order to obtain the desired metal content.

It is also possible, for example, to prepare an aqueous $Ni(CO_3)_2$ solution or ammoniacal $Pd(NO_3)_2$ solution and to suspend the pure zeolite powder therein at from 40° to 100° C. for about 24 hours, while stirring. After the product has been filtered off, dried at about 150° C. and calcined at about 500° C., the zeolite material thus obtained can be further processed with or without a binder to give extrudates, pellets or fluidizable material.

The zeolite in the H form or ammonium form or alkali metal form can be subjected to ion exchange by a method in which the zeolite, in the form of extrudates or pellets, is initially taken in a column and, for example, an aqueous $Ni(NO_3)_2$ solution or ammoniacal $Pd(NO_3)_2$ solution is circulated over the said zeolite at slightly elevated temperatures of from 30° to 80° C. for from 15 to 20 hours. Thereafter, the product is washed thoroughly with water, dried at about 150° C. and calcined at about 550° C. In the case of some metal-doped zeolites, for example Pd-, Cu- or Ni-doped zeolites, an aftertreatment with hydrogen is advantageous.

In another possible method of modification, the molded or unmolded zeolite is subjected to a treatment with acids, such as hydrochloric acid, hydrofluoric acid and phosphoric acid and/or steam. In this procedure, a zeolite in powder form is advantageously treated with 1 N phosphoric acid for 1 hour at 80° C. After the treatment, the product is washed with water, dried at 110° C. for 16 hours and calcined at 500° C. for 20 hours. In another procedure, the zeolite, before or after it has been molded with a binder, is treated with a 3–25% strength by weight aqueous hydrochloric acid for from 1 to 3 hours at from 60° to 80° C. The zeolite treated in this manner is then washed with water, dried, and calcined at from 400° to 500° C.

In a particular embodiment of the acid treatment, the zeolite material, before it has been molded, is treated at elevated temperatures with hydrofluoric acid, which is generally used in the form of 0.001-2 N, preferably 0.05–0.5 N, hydrofluoric acid, for example by refluxing for from 0.5 to 5, preferably from 1 to 3, hours. After the zeolite material has been isolated, for example by filtering it off and washing it thoroughly, it is advantageously dried at from 100° to 160° C. and calcined at from 450° to 600° C. In another embodiment, the zeolite material, after it has been molded with a binder, can be treated at elevated temperatures, for example from 50° to 90° C., preferably from 60° to 80° C., for from 0.5 to 5 hours, with 12–20% strength by weight hydrochloric acid. The zeolite material is then generally washed thoroughly, dried at from 100° to 160° C. and calcined at from 450° to 600° C. An HF treatment may furthermore be followed by treatment with HCL.

In another procedure, zeolites can be modified by applying phosphorus compounds, such as trimethoxyphosphate, trimethoxyphosphine or primary, secondary or tertiary sodium phosphate. Treatment with primary sodium phosphate has proven particularly advantageous. In this procedure, the zeolite in the form of extrudates, pellets or fluidizable material is impregnated with aqueous $NaH_2PO_4$ solution, dried at 110° C. and calcined at 500° C.

Other heterogeneous catalysts for the novel process are phosphates, in particular aluminum phosphates, silicon aluminum phosphates, silicon iron aluminum phosphate, cerium phosphate, zirconium phosphates, boron phosphate, iron phosphate or mixtures of these.

In particular, aluminum phosphates synthesized under hydrothermal conditions are used as aluminum phosphate catalysts for the novel process.

The aluminum phosphates prepared under hydrothermal conditions are, for example, APO-5, APO-9, APO11, APO-12, APO-14, APO-21, APO-25, APO-31 and APO-33. Syntheses of these compounds are described in European Pat. No. 132,708 and U.S. Pat. Nos. 4,310,440 and 4,473,663.

For example, $AlPO_4{-}^5$ (APO-5) is synthesized by a method in which orthophosphoric acid is homogeneously mixed with pseudoboehmite (CATAPAL SB®) in water, tetrapropyl ammonium hydroxide is added to this mixture, and the reaction is then carried out at about 150° C. for from 20 to 60 hours under autogenous pressure in an autoclave. The $AlPO_4$ filtered off is dried at from 100° to 160° C. and calcined at from 450° to 550° C.

AlPO$_4$$^{-9}$ (APO-9) is likewise synthesized from orthophosporic acid and pseudoboehmite, but in aqueous DABCO solution (1,4-diazabicyclo[2.2.2]octane) at about 200° C. under autogenous pressure in the course of from 200 to 400 hours.

AlPO$_4$$^{-21}$ (APO-21) is synthesized from orthophosphoric acid and pseudoboehmite in aqueous pyrrolidone solution at from 150° to 200° C. under autogenous pressure in the course of from 50 to 200 hours.

The silicon aluminum phosphates used for the novel process are, for example, SAPO-5, SAPO-11, SAPO-31 and SAPO-34. The synthesis of this compound is described in for example, European Patent 103,117 and U.S. Patent 4,440,871. SAPOs are prepared by crystallization from an aqueous mixture at from 100 to 250° C. and under autogeneous pressure in the course of from 2 hours to 2 weeks, the reaction mixture of a silicon component, an aluminum component and a phosphorus component being reacted in aqueous solutions containing organic amines.

For example, SAPO-5 is obtained by mixing SiO$_2$, suspended in aqueous tetrapropylammonium hydroxide solution, with an aqueous suspension of pseudoboehmite and orthophosphoric acid, and then carrying out the reaction at from 150° to 200° C. in the course of from 20 to 200 hours under autogenous pressure in a stirred autoclave. The powder which has been filtered off is dried at from 110° to 160° C. and calcined at from 450° to 550° C.

Precipitated aluminum phosphates may also be employed as phosphate catalysts in the process. For example, an aluminum phosphate of this type is prepared by dissolving 92 g of diammonium hydrogen phosphate in 700 ml of water. 260 g of Al(NO$_3$)$_3$. H$_2$O in 700 ml of water are added dropwise to this solution in the course of 2 hours. During this procedure, the pH is kept at 8 by the simultaneous addition of 25% strength NH$_3$ solution. The resulting precipitate is stirred for a further 12 hours and then filtered off under suction, washed thoroughly and then dried at 60° C. for 16 hours.

Boron phosphates for the novel process can be prepared, for example, by mixing and kneading concentrated boric acid and phosphoric acid and by subsequent drying and Falcination in an inert gas, air or steam atmosphere at from 250° to 650° C., preferably from 300° to 500° C.

Modifying components as described above in the case of the zeolites can be applied to these phosphates by impregnation (immersion or spraying on) or, in some cases, by ion exchange. Modification with acids can also be carried out, as in the case of the zeolite catalysts.

The catalysts described here can be used alternatively in the form of 2-4 mm extrudates, tablets of 3-5 mm diameter or chips having particle sizes of from 0.1 to 0.5 mm or as a fluidizable catalyst.

The novel reaction is preferably carried out in the gas phase or in the supercritical range from 100° to 500° C., in particular from 200° to 400° C., using a WHSV of from 0.1 to 20 h$^{-1}$, preferably from 0.5 to 5 h$^{-1}$ (g of starting material per g of catalyst per hour). The molar ratio of unsaturated organic compound to PH-containing phosphorus compound is from 6:1 to 1:20, preferably from 3:1 to 1:5. The reaction can be carried out in a fixed bed or fluidized bed.

It is also possible to carry out the reaction in the liquid phase (suspension, trickle-bed or liquid-phase procedure) at from $-20°$ to 200° C.

The process is carried out under atmospheric pressure or under superatmospheric pressures of from 0.5 to 500 bar, depending on the volatility of the starting compound, and is preferably effected continuously, although a batchwise procedure is also possible.

Sparingly volatile or solid starting materials are used in dissolved form, for example in solution in tetrahydrofuran, toluene or petroleum ether. In general, the starting material may be diluted with solvents of this type or with inert gases, such as N$_2$, Ar or steam.

After the reaction, the resulting products are isolated by a conventional method, for example by distillation from the reaction mixture; unconverted starting materials may be recycled to the reaction.

It is particularly advantageous to analyze the gaseous reaction mixture immediately and then to separate it into the individual components. A separation of this type can be carried out, for example, in a fractionating column.

The Examples which follow illustrate the invention.

EXAMPLES 1-20

The reaction is carried out under isothermal conditions in a metal autoclave or in glass ampoules. The reaction products are separated by a conventional method, for example in an apparatus under greatly reduced pressure, and are characterized by IR, NMR and MS spectroscopy. Quantitative determination of the reaction products and of the starting materials is carried out by gas chromatography or by weighing. In the experiments below, the batches were chosen so that the glass ampoule contained 75 millimoles of the starting mixture. This gave a reaction pressure of 8 bar at 100° C. and 190 bar at 200° C.

The catalysts used for the novel process are:

Catalyst A

The borosilicate zeolite of the pentasil type is prepared in a hydrothermal synthesis from 640 g of finely divided SiO$_2$, 122 g of H$_3$BO$_3$ and 8,000 g of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of SiO$_2$ and 2.3% by weight of B$_2$O$_3$.

This material is molded with a molding assistant to give 2 mm extrudates, which are dried at 110° C. for 16 hours and calcined at 500° C. for 24 hours.

Catalyst B

An aluminosilicate zeolite of the pentasil type is prepared under hydrothermal conditions, under autogenous pressure and at 150° C., from 65 g of finely divided SiO$_2$ and 20.3 g of Al$_2$(SO$_4$)$_3$. 18 H$_2$O in 1 kg of an aqueous 1,6-hexanediamine solution (weight ratio 50:50) in a stirred autoclave. The crystalline reaction product is filtered off, washed thoroughly, dried at 110° C. for 24 hours and then calcined at 500° C. for 24 hours. This aluminosilicate zeolite contains 91.6% by weight of SiO$_2$ and 4.6% by weight of Al$_2$O$_3$. The catalyst is molded with a molding assistant to give 2 mm extrudates, which are dried at 110° C. for 16 hours and calcined at 500° C. for 24 hours.

Catalyst C

Catalyst C is obtained by impregnating the extrudates of catalyst A with an aqueous $Cr(NO_3)_3$ solution and then drying the product at 130° C. for 2 hours and calcining it at 540° C. for 2 hours. The Cr content is 1.9% by weight.

Catalyst D

The iron silicate zeolite of the pentasil type is synthesized under hydrothermal conditions, under autogeneous pressure and at 165° C., from 273 g of waterglass, dissolved in 253 g of an aqueous 1,6-hexanediamine solution (weight ratio 50 : 50), and 31 g of iron sulfate, dissolved in 21 g of 96% strength sulfuric acid and 425 g of water, in a stirred autoclave in the course of 4 days. The zeolite formed is filtered off, washed thoroughly, dried at 110° C. for 24 hours and calcined at 500° C. for 24 hours. An iron silicate zeolite having an $SiO_2/Fe_2O_3$ ratio of 17.7 and a $Na_2O$ content of 1.2% by weight is obtained. The catalyst is extruded with finely divided $SiO_2$ in a weight ratio of 70:30 to give 2.5 mm extrudates, which are dried at 110° C. for 16 hours and calcined at 500° C. for 24 hours. These extrudates are subjected to ion exchange with a 20% by weight strength $NH_4Cl$ solution at 80° C. and then washed chloride-free, dried at 110° C., and calcined at 500° C. for 5 hours. Ion exchange is continued until the Na content is 0.002% by weight.

Catalyst E

Catalyst E is prepared in the same manner as catalyst C, except that $Cr(NO_3)_3$ is replaced with $Ce(NO_3)_3$. The Ce content is 1.7% by weight.

Catalyst F

Silicon aluminum phosphate-5 (SAPO-5) is prepared from a mixture of 200 g of 98% strength phosphoric acid, 136 g of boehmite, 60 g of silica sol (30% strength), 287 g of tripropylamine and 587 g of $H_2O$. This mixture is reacted at 15° C. in the course of 168 hours under autogenous pressure. The crystalline product is filtered off, dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with an extrusion assistant to give 3 mm extrudates, which are dried at 120° C. and calcined at 500° C.

Catalyst G

Commercial zirconium phosphate, $Zr_3(PO_4)_4$, molded in pure form.

Catalyst H $BPO_4$ is prepared by combining 49 g of $H_3BO_4$ with 117 g of $H_3PO_4$ (75% strength) in a kneader, evaporating off excess water and molding the reaction product to give 3 mm extrudates. These extrudates are dried at 100° C. and calcined at 350° C. Catalyst H contains 8.77% by weight of B and 28.3% by weight of P.

The experimental results obtained with these catalysts and the experimental conditions are summarized in Table 1.

TABLE 1

| Example | Catalyst | Educt I | Educt II | Molar ratio I/II | Temperature [°C.] | Product | Conversion [%] | Selectivity [%] |
|---------|----------|---------|----------|------------------|-------------------|---------|----------------|-----------------|
| 1 | A | $PH_3$ | $\rangle\!=$ | 2:1 | 200 | $\rangle\!-\!PH_2$ | 62 | 85 |
| 2 | A | " | " | " | 100 | " | 42 | 98 |
| 3 | C | " | " | " | 200 | " | 70 | 90 |
| 4 | B | " | " | " | 100 | " | 15 | 95 |
| 5 | D | " | " | " | 100 | " | 32 | 83 |
| 6 | A | $H_3CPH_2$ | " | " | 100 | $\rangle\!-\!PHCH_3$ | 41 | 92 |
| 7 | B | " | " | " | 100 | " | 39 | 91 |
| 8 | E | " | " | " | 100 | " | 21 | 70 |
| 9 | C | " | " | 1:3 | 100 | " | 20 | 89 |
| 10 | C | $PH_3$ | ⁀ | 1:1 | 200 | $\rangle\!-\!PH_2$ | 16 | 84 |
| 11 | C | $H_3CPH_2$ | " | 1:4 | 200 | $\rangle\!-\!PHCH_3$ | 18 | 85 |
| 12 | C | $PH_3$ | $C_2H_4$ | 1:1 | 200 | $C_2H_5PH_2$ | 7 | 80 |
| 13 | C | $PH_3$ | ⬠ | 2:1 | 100 | ⬠$-PH_2$ | 10 | 85 |
| 14 | C | " | ⬡ | 2:1 | 100 | ⬡$-PH_2$ | 12 | 81 |

TABLE 1-continued

| Example | Catalyst | Educt I | Educt II | Molar ratio I/II | Temperature [°C.] | Product | Conversion [%] | Selectivity [%] |
|---|---|---|---|---|---|---|---|---|
| 15 | C | " | (diene) | 2:1 | 100 | ⟶PH₂⁽¹⁾ | 19 | 79 |
| 16 | C | " | (cyclohexadiene) | 2:1 | 100 | cyclohexenyl-PH₂⁽¹⁾ | 20 | 75 |
| 17 | F | " | isobutylene | 2:1 | 100 | t-Bu-PH₂ | 15 | 87 |
| 18 | G | " | " | 2:1 | 100 | " | 18 | 78 |
| 19 | H | " | " | 2:1 | 100 | " | 25 | 82 |
| 20 | H | CH₃PH₂ | " | 2:1 | 100 | t-Bu-PHCH₃ | 7 | 71 |

⁽¹⁾Including all isomers

We claim:

1. A process for the preparation of an organophosphorus compound which comprises: subjecting an olefinically unsaturated compound, selected from the group consisting of an unsaturated straight-chain, branched or cyclic olefin, a diene having conjugated or nonconjugated double bonds and mixtures thereof, to an addition reaction with a phosphine-containing compound selected from the group consisting of phosphine, primary or secondary phosphines, diphosphanes, polyphosphanes, organophosphorus oxides and mixtures thereof, by contacting the loefinically unsaturated compound and the phosphine-containing compound in a molar ratio of from 6:1 to 1:20, in the presence of a zeolite catalyst and mixtures thereof in acidic form, at a temperature of 100° C. to 500° C., and isolating the organophosphorous compound produced by the addition reaction.

2. A process as claimed in claim 1, wherein a zeolite of the pentasil type is used as the catalyst.

3. A process as claimed in claim 1, wherein an aluminosilicate zeolite and/or a borosilicate zeolite and/or an iron silicate zeolite of the pentasil type are used as the catalyst.

4. A process as claimed in claim 1, wherein a zeolite of the faujasite type is used as the catalyst.

5. A process as claimed in claim 1, wherein a zeolite doped with an alkali metal, a transition metal or a rare earth metal is used as the catalyst.

6. A process as claimed in claim 1, wherein the reaction is carried out in the gas phase or in the supercritical range.

* * * * *